(12) United States Patent
Li

(10) Patent No.: US 7,255,884 B2
(45) Date of Patent: Aug. 14, 2007

(54) COMPOSITION FOR TREATMENT OF ASTHMA

(76) Inventor: Hongfen Li, 1/39 Einstein St., Rama-Aviv Tel-Aviv (IL)

( * ) Notice: Subject to any disclaimer, the term of this patent is extended or adjusted under 35 U.S.C. 154(b) by 487 days.

(21) Appl. No.: 10/683,984

(22) Filed: Oct. 2, 2003

(65) Prior Publication Data

US 2004/0071796 A1 Apr. 15, 2004

Related U.S. Application Data

(63) Continuation of application No. PCT/CN01/01522, filed on Nov. 1, 2001.

(30) Foreign Application Priority Data

Apr. 2, 2001 (IL) ..................................... 135447

(51) Int. Cl.
*A61K 36/00* (2006.01)
*A61K 36/236* (2006.01)
*A61K 36/718* (2006.01)
*A61K 36/736* (2006.01)

(52) U.S. Cl. ..................... 424/725; 424/735; 424/741; 424/757; 424/773; 424/774; 424/775; 424/778

(58) Field of Classification Search ............. 424/195.1, 424/725

See application file for complete search history.

(56) References Cited

U.S. PATENT DOCUMENTS

2002/0031559 A1 * 3/2002 Liang et al. ................ 424/725

* cited by examiner

*Primary Examiner*—Patricia Leith
(74) *Attorney, Agent, or Firm*—Brouse McDowell; Roger D. Emerson; Daniel A. Thomson

(57) ABSTRACT

A pharmaceutical preparation of Chinese herbal medicines for tonifying the kidneys and alleviating asthma is disclosed herein. The Chinese herbal medicines include *Perilla Frutescens, Prunus Armeniaca, Glycyrrhiza Uralensis, Scutellaria Baicalensis, Coptis Chinesis, Tusilago Farfara, Stemona Sessilifolia, Fritillaria Cirrhosa, Pheretima Aspergillum, Psoralaea Corylifolia, Codonopsis Pilosula, Hordeum Vulgara, Massa Fermentata Medicalis, Schisandra Chinesis*, and *Gypsum*. The preparation is used to treat thousands of patients suffering from asthma with an effective rate of 93%. The present preparation can relieve cough, expel phlegm, resist airway allergic inflammation reaction, improve pulmonary function, partial pressure of the oxygen in the blood, increase $CD_2$, $CD_4$, $CD_4/CD_8$, reduce $I_gE$ in blood, increase CAMP, reduce CGMP, stabilize mast cells, and inhibit the release of histamine, which make it capable of stopping an asthma attack.

10 Claims, No Drawings

COMPOSITION FOR TREATMENT OF ASTHMA

This application is a continuation of, and claims priority under 35 U.S.C. §120 to, PCT/CN01/01522, filed Nov. 1, 2001.

FIELD OF THE INVENTION

The present invention relates to a composition for the treatment of asthma. More particularly, the present invention relates to a composition for treating asthma made from Chinese herbal medicine.

BACKGROUND OF THE INVENTION

Several studies have indicated that the prevalence rate of asthma is increasing in many regions while the morbidity rate remains high. Despite progress in the research concerning pathogenesis mechanism and therapy for asthma, morbidity rate and even mortality rate of this disease in the advanced country is increasing. At present, the preventive therapy for the asthma is mainly based on systemic corticosteroids administrated by inhalation and oral route. But the significant adverse effects were found with long—term use of hormone. Therefore patients often express interest to exploit non-Western Medicine approaches to prevent and relieve symptom of asthma. In China, herbal therapy has been used for several centuries as therapy for asthma with significantly beneficial effects. Since the composition of herbs is not standardized and is individualized for each patient with adding or reducing the components therein. But the previous formulas were used to treat asthma only for one side, for example only for asthma attack or only for prevention.

CONTENT OF THE INVENTION

Based on long term research, the inventor finds the following prescriptions (PCCJ) are useful in attack period and catabasis of asthma. The compositions are made of both of the medicines for anti-asthma attack and those for preventing asthma (combination of herbal medicines for tonifying kidney and those for eliminating pathogenic factors), and specially are made from a part or all of the following Chinese herbal medicine: Ma Huang (*EPHEDRA SINICA*), Xing Ren (*PRUNUS ARMENIACA*), Gan Cao (*GLYCYRRHIZA URALENSIS*), Huang Qin (*SCUTELLARIA BAICALENSIS*), Huang Lian (*COPTIS CHINESIS*), Huang Bai (*PHELLODENDRON CHINENSE*), Kuan Dong Hua (*TUSILAGO FARFARA*), Bai Bu (*STEMONA SESSILIFOLIA*), Chuan Bei Mu (or Bei Mu) (*FRITILLARIA CIRRHOSA*), Di Long (*PHERETIMA ASPERGILLUM*), BU Gu Zhi (*PSORALEA CORYLIFOLIA*), Dang Shen (*CODONOPSIS PILOSULA*), Shan Zha (*CRATAEGUS PINNATIFIDA*), Mai Ya (*HORDEUM VULGARE*), Shen Qu (*MASSA FERMENTATA MEDICINALIS*), Wu Wei Zi (*SCHISANDRA CHINENSIS*), Shi Gao (*GYPSUM*), Su Zi (*FERILLA FRUTESCENS*), Zi Wan (*ASTER TATARICUS*), Bai Shao (*PAEONIA LACTIFLORA*), Jin Yin Hua (*LONICERA JAPONICA*), Lian Qiao (*FORSYTHIA SUSPENSA*), Jing Jie (*SCHIZONEPETA TENUIFOLIA*), Huang Qi (*ASTRAGALUS MEMBRANACEUS*), Fang Feng (*LEDEBOURIELLA DIVARICATA*).

From above list of Chinese herbal medicines, the following 7 specific prescriptions are preferable, in which Prescription 1 is basic one (research formula) and Prescriptions 2 to 6 are adding or reducing ones.

PRESCRIPTION 1

| Name (pinyin) | Latin Name (species) | % amount (w/w) |
|---|---|---|
| MA HUANG | EPHEDRA SINICA | 5.1% |
| XING REN | PRUNUS ARMENIACA | 6.12% |
| GAN CAO | GLYCYRRHIZA URALENSIS | 5.1% |
| HUANG QIN | SCUTELLARIA BAICALENSIS | 6.12% |
| HUANG LIAN | COPTIS CHINESIS | 6.12% |
| HUANG BAI | PHELLODENDRON CHINENSE | 6.12% |
| KUANG DONG HUA | TUSILAGO FARFARA | 5.1% |
| BAI BU | STEMONA SESSILIFOLIA | 5.1% |
| CHUAN BEI MU | FRITILLARIA CIRRHOSA | 5.1% |
| DI LONG | PHERETIMA ASPERGILLUM | 5.1% |
| BU GU ZHI | PSORALEA CORYLIFOLIA | 5.1% |
| DANG SHEN | CODONOPSIS PILOSULA | 6.12% |
| SHAN ZHA | CRATAEGUS PINNATIFIDA | 4.1% |
| MAI YA | HORDEUM VULGARE | 2.04% |
| SHEN QU | MASSA FERMENTATA MEDICINALIS | 2.04% |
| WU WEI ZI | SCHISANDRA CHINENSIS | 5.1% |
| SHI GAO | GYPSUM | 15.31% |
| SU ZI | PERILLA FRUTESCENS | 5.1% |

PRESCRIPTION 2

| Name (pinyin) | Latin Name (species) | % amount (w/w) |
|---|---|---|
| MA HUANG | EPHEDRA SINICA | 5.1(1-10)% |
| XING REN | PRUNUS ARMENIACA | 6.12(1-10)% |
| GAN CAO | GLYCYRRHIZA URALENSIS | 5.1(1-10)% |
| HUANG QIN | SCUTELLARIA BAICALENSIS | 6.12(1-10)% |
| HUANG LIAN | COPTIS CHINESIS | 6.12(1-15)% |
| HUANG BAI | PHELLODENRON CHINENSE | 6.12(1-15)% |
| KUANG DONG HUA | TUSILAGO FARFARA | 5.1(1-10)% |
| BAI BU | STEMONA SESSILIFOLIA | 5.1(1-10)% |
| CHUAN BEI MU | FRITILLARIA CIRRHOSA | 5.1(1-10)% |
| DI LONG | PHERETIMA ASPERGILLUM | 5.1(1-15)% |
| BU GU ZHI | PSORALEA CORYLIFOLIA | 5.1(1-10)% |
| DANG SHEN | CODONOPSIS PILOSULA | 6.12(1-10)% |
| SHAN ZHA | CRATAEGUS PINNATIFIDA | 4.1(1-8)% |
| MAI YA | HORDEUM VULGARE | 2.04(1-6)% |
| SHEN QU | MASSA FERMENTATA MEDICINALIS | 2.04(1-6)% |
| WU WEI ZI | SCHISANDRA CHINENSIS | 5.1(1-10)% |
| SHI GAO | GYPSUM | 15.31(5-30)% |
| SU ZI | PERILLA FRUTESCENS | 5.1(1-10)% |

PRESCRIPTION 3

| Name (pinyin) | Latin Name (species) | % amount (w/w) |
|---|---|---|
| MA HUANG | *EPHEDRA SINICA* | 5.1(1-30)% |
| XING REN | *PRUNUS ARMENIACA* | 6.12(1-30)% |
| GAN CAO | *GLYCYRRHIZA URALENSIS* | 5.1(1-30)% |
| HUANG QIN | *SCUTELLARIA BAICALENSIS* | 6.12(1-35)% |
| HUANG LIAN | *COPTIS CHINESIS* | 6.12(1-35)% |
| HUANG BAI | *PHELLODENRON CHINENSE* | 6.12(1-35)% |
| KUANG DONG HUA | *TUSILAGO FARFARA* | 5.1(1-30)% |
| BAI BU | *STEMONA SESSILIFOLIA* | 5.1(1-30)% |
| CHUAN BEI MU | *FRITILLARIA CIRRHOSA* | 5.1(1-30)% |
| DI LONG | *PHERETIMA ASPERGILLUM* | 5.1(1-35)% |
| BU GU ZHI | *PSORALEA CORYLIFOLIA* | 5.1(1-30)% |
| DANG SHEN | *CODONOPSIS PILOSULA* | 6.12(1-30)% |
| SHAN ZHA | *CRATAEGUS PINNATIFIDA* | 4.1(1-30)% |
| MAI YA | *HORDEUM VULGARE* | 2.04(1-30)% |
| SHEN QU | *MASSA FERMENTATA MEDICINALIS* | 2.04(1-30)% |
| WU WEI ZI | *SCHISANDRA CHINENSIS* | 5.1(1-30)% |
| SHI GAO | *GYPSUM* | 15.31(5-50)% |
| SU ZI | *PERILLA FRUTESCENS* | 5.1(1-30)% |

PRESCRIPTION 4

| Name (pinyin) | Latin Name (species) | % amount (w/w) |
|---|---|---|
| XING REN | *PRUNUS ARMENIACA* | 6.12(1-30)% |
| GAN CAO | *GLYCYRRHIZA URALENSIS* | 6(1-30)% |
| HUANG QIN | *SCUTELLARIA BAICALENSIS* | 6.12(1-35)% |
| HUANG LIAN | *COPTIS CHINESIS* | 6.12(1-35)% |
| ZI WAN | *ASTER TATARICUS* | 5.1(1-30)% |
| BAI BU | *STEMONA SESSILIFOLIA* | 5.1(1-30)% |
| BEI MU | *FRITILLARIA CIRRHOSA* | 5.1(1-30)% |
| DI LONG | *PHERETIMA ASPERGILLUM* | 5.1(1-35)% |
| BU GU ZHI | *PSORALEA CORYLIFOLIA* | 5.1(1-30)% |
| DANG SHEN | *CODONOPSIS PILOSULA* | 6.12(1-30)% |
| SHAN ZHA | *CRATAEGUS PINNATIFIDA* | 4.1(1-30)% |
| MAI YA | *HORDEUM VULGARE* | 2.04(1-30)% |
| SHEN QU | *MASSA FERMENTATA MEDICINALIS* | 2.04(1-30)% |
| WU WEI ZI | *SCHISANDRA CHINENSIS* | 5.1(1-30)% |
| SHI GAO | *GYPSUM* | 15.31(1-50)% |
| SU ZI | *PERILLA FRUTESCENS* | 5.1(1-30)% |

In the prescription, BAI SHAO (PAEONIA LACTIFLORA) can be added in the amount of 4(1-30)%.

PRESCRIPTION 5

| Name (pinyin) | Latin Name (species) | % amount (w/w) |
|---|---|---|
| XING REN | *PRUNUS ARMENIACA* | 6.12(1-30)% |
| GAN CAO | *ASTER TATARICUS* | 6(1-30)% |
| HUANG QIN | *SCUTELLARIA BAICALENSIS* | 6.12(1-35)% |
| HUANG LIAN | *COPTIS CHINESIS* | 6.12(1-35)% |
| HUANG BAI | *PHELLODENRON CHINENSE* | 6.12(1-35)% |
| KUANG DONG HUA | *TUSILAGO FARFARA* | 5.1(1-30)% |
| BAI BU | *STEMONA SESSILIFOLIA* | 5.1(1-30)% |
| BEI MU | *FRITILLARIA CIRRHOSA* | 5.1(1-30)% |
| DI LONG | *PHERETIMA ASPERGILLUM* | 5.1(1-35)% |
| BU GU ZHI | *PSORALEA CORYLIFOLIA* | 5.1(1-30)% |
| DANG SHEN | *CODONOPSIS PILOSULA* | 6.12(1-30)% |
| SHAN ZHA | *CRATAEGUS PINNATIFIDA* | 4.1(1-30)% |
| MAI YA | *HORDEUM VULGARE* | 2.04(1-30)% |
| SHEN QU | *MASSA FERMENTATA MEDICINALIS* | 2.04(1-30)% |
| WU WEI ZI | *SCHISANDRA CHINENSIS* | 5.1(1-30)% |
| SHI GAO | *GYPSUM* | 15.31(1-50)% |
| SU ZI | *PERILLA FRUTESCENS* | 5.1(1-30)% |
| BAI SHAO | *PAEONIA LACTIFLORA* | 4(1-30)% |

PRESCRIPTION 6

| Name (pinyin) | Latin Name (species) | % amount (w/w) |
| --- | --- | --- |
| XING REN | *PRUNUS ARMENIACA* | 6.12(1-30)% |
| GAN CAO | *ASTER TATARICUS* | 5.1(1-30)% |
| HUANG QIN | *SCUTELLARIA BAICALENSIS* | 6.12(1-35)% |
| HUANG LIAN | *COPTIS CHINESIS* | 6.12(1-35)% |
| BAI BU | *STEMONA SESSILIFOLIA* | 5.1(1-30)% |
| CHUAN BEI MU | *FRITILLARIA CIRRHOSA* | 5.1(1-30)% |
| DI LONG | *PHERETIMA ASPERGILLUM* | 5.1(1-35)% |
| BU GU ZHI | *PSORALEA CORYLIFOLIA* | 5.1(1-30)% |
| DANG SHEN | *CODONOPSIS PILOSULA* | 6.12(1-30)% |
| SHAN ZHA | *CRATAEGUS PINNATIFIDA* | 4.1(1-30)% |
| MAI YA | *HORDEUM VULGARE* | 2.04(1-30)% |
| SHEN QU | *MASSA FERMENTATA MEDICINALIS* | 2.04(1-30)% |
| WU WEI ZI | *SCHISANDRA CHINENSIS* | 5.1(1-30)% |
| SHI GAO | *GYPSUM* | 15.31(5-50)% |
| SU ZI | *PERILLA FRUTESCENS* | 5.1(1-30)% |
| BAI SHAO | *PAEONIA LACTIFLORA* | 4(1-30)% |
| JIN YIN HUA | *LONICERA JAPONICA* | 5(1-30)% |
| LIAN QIAO | *FORSYTHIA SUSPENSA* | 6(1-30)% |
| JING JIE | *SCHIZONEPETA TENUIFOLIA* | 5(1-30)% |

PRESCRIPTION 7

| Name (pinyin) | Latin Name (species) | % amount (w/w) |
| --- | --- | --- |
| XING REN | *PRUNUS ARMENIACA* | 6.12(1-30)% |
| GAN CAO | *ASTER TATARICUS* | 5.1(1-30)% |
| HUANG QIN | *SCUTELLARIA BAICALENSIS* | 6.12(1-35)% |
| HUANG LIAN | *COPTIS CHINESIS* | 6.12(1-35)% |
| BAI BU | *STEMONA SESSILIFOLIA* | 5.1(1-30)% |
| CHUAN BEI MU | *FRITILLARIA CIRRHOSA* | 5.1(1-30)% |
| DI LONG | *PHERETIMA ASPERGILLUM* | 5.1(1-35)% |
| BU GU ZHI | *PSORALEA CORYLIFOLIA* | 5.1(1-30)% |
| DANG SHEN | *CODONOPSIS PILOSULA* | 6.12(1-30)% |
| SHAN ZHA | *CRATAEGUS PINNATIFIDA* | 4.1(1-30)% |
| MAI YA | *HORDEUM VULGARE* | 2.04(1-30)% |
| SHEN QU | *MASSA FERMENTATA MEDICINALIS* | 2.04(1-30)% |
| WU WEL ZI | *SCHISANDRA CHINENSIS* | 5.1(1-30)% |
| SHI GAO | *GYPSUM* | 15.31(5-50)% |
| SU ZI | *PERILLA FRUTESCENS* | 5.1(1-30)% |
| BAI SHAO | *PAEONIA LACTIFLORA* | 4(1-30)% |
| HUANG QI | *ASTRAGALUS MEMBRANACEUS* | 6(1-30)% |
| FANG FENG | *LEDEBOURIELLA DIVARICATA* | 5(1-30)% |
| JIN YIN HUA | *LONICERA JAPONICA* | 5(1-30)% |
| LIAN QIAO | *FORSYTHIA SUSPENSA* | 6(1-30)% |
| JING JIE | *SCHIZONEPETA TENUIFOLIA* | 5(1-30)% |

In the prescription, JIN YIN HUA (*LONICERA JAPONICA*) LIAN QIAO (*FORSYTHIA SUSPENSA*)) JING JIE (*SCHIZONEPETA TENUIFOLIA*) can be canceled.

Note: In each above-mentioned prescriptions, the figures shown in parenthesis represent that the percentage amount can vary within the range, for example, (1-30) in LIAN QIAO 6(1-30) % means that the percentage amount of LIAN QIAO can vary from 1 to 30.

These formulas can be formulated into various dosage forms, for example, the herbs can be ground into powder, mix homogeneously and then encapsulated into capsules with 0.5 g per capsule. Also, the formulas can formulated into infusion according to various conventional processes. All of these dosage forms can reach good effects.

These prescriptions are based on Ma Xing Shi Gan Tang (Decoction of Ephedra, Apricot, Gypsum and Licorice) and Huang Lian Jie Du Tang (Antidotal Decoction of coptis), and are formed by modification. Among the various components of prescription, Ma Huang acts as a principle drug, and exert the effect of facilitating the flow of Lung-Qi to relive asthma, and its pungent flavor is good at dispelling exogenous factors. Shi Gao plays the role of an assistant drug with the effects of both clearing and purging Lung-heat to restrict the warm property of Ma Huang, Xing Ren, a drug with a bitter taste and warm property, is used as adjuvant drug to reinforce Ma Huang and Shi Gao in facilitating the flow of the lung-qi to relieve asthma. Gan Cao is used as a guiding drug for replenishing Qi and regulating the middle-warmer, and coordinating the effect of various drugs in case of the cold and heavy property of Shi Gao impairs the stomach. In the Huanglian Jiedu Tang, ingredient Huang Lian is used as principal drug, which plays a significant role of purging pathogenic fire in the heart and middle-energizer; Huang Qin acts as an assistant drug with the effect of clearing away heat in the lung and purging fire in the upper-energizer; Huang Bai is used as both adjuvant and guiding drugs, the former provides the effect of purging pathogenic fire in lower-energizer and the latter have the effect of removing pathogenic fire in the tri-energizer by inducing diuresis. In the prescriptions of the present invention, Su Zi relieves cough and asthma, descends Qi to remove phlegm, and moistening intestines to loosen the bowels, which is used together with Xing Ren; Kuan Dong Hua moistens the lung and lowers Qi, resolves phlegm and relieves cough and assists Xing Ren and Bei Mu; Bai Bu and Bei Mu resolve phlegm to stop cough; Di Long expels wind to relieve spasm, expand bronchus, clear away heat from lung to relieve asthma, which is used with Ma Huang, Xing Ren and Shi Gao; Wu Wei Zi astringes the lung and nourishes the kidney; Dang Shen invigorates the spleen and replenishes the Qi and is useful for insufficiency of the lung-qi consumption; Bu Gu Zhi tonifys the kidney and strengthen the Yang, which is used with Dang Shen and Wu Wei Zi to astringe the lung-qi; Shan Zha, Mai ya, and Shen Qu strength the spleen and improve digestion in order to prevent the drugs for replenishing Qi and blood (Yi Qi Bu Xue Yao) from growing loathful Qi to block the spleen and stomach's function of transport and digestion. The various components in the prescriptions corporate each other so that the action of the whole formula is tonifying but not stagnant, and is purgation but not asthenia. So the formulas increase organism's immunity function and dilate bronchi to stop asthma.

THE BENEFICIAL EFFECT OF THE INVENTION

The composition of the present invention can be formulated into capsule and infusion, in which Asthma-Relieving Infusion (Ping Chuan Chong Ji, hereinafter referred to as simply PCCJ), a dosage form of above-mention prescriptions prepared according to various conventional technologies, has been used for more than 20 years in China and more than 5 years in Israel. The treatment of bronchial asthma can be divided into two stages: attack stage and remission stage. During the attack stage, the curative effect of PCCJ is not faster than those of western medicines, but it is better than western medicines in the remission stage. The principle lies in that the treatment of cough and dyspnea concerns not only lung but also kidney, and the symptoms of lung are treated in the attack stage, while therapies for tonifying kidney are applied in the remission stage. Based on the whole body, PCCJ pays more attention to elaborating the body potential energy and strengthening the body resistance to the disease, therefore it can be useful for treating the allergic and non-allergic asthma. The morbidity rate of asthma has been getting higher year by year in the past ten years, which may be related to the misunderstanding of asthmatic pathogenesis and wrong therapy. In the past years, it is the classical pathologic theory that bronchospasm is the main pathologic change of asthma. The new concept of asthma's pathologic mechanism put forward by some universities is that airway allergic inflammation is the pathologic change of asthma, and it is found in airway lavage solution that there are more eosinocytes and macrophages than mast cell, which induce the attack of asthma easier. Among inflammatory mediators, the bioactivity of platelet activating factor (PAF) is much stronger than those of interleukin, prostaglandin as well as histamine, whose pathogenic effect is 1000 times stronger than that of histamine, thus it is the eosinophilic chemotactic factor with stronger activity. The bronchodilator has been used as the first therapy of bronchus asthma for forty years. Studies have showed that the high sensitive state of bronchus is the main reason for the worsening of asthma because a long-term use of bronchodilator may conceal the development of inflammation to cause the patients' symptom worsened, which is the main reason why asthmatic mortality is increasing year by year. At present, adrenal cortical hormone is an effective anti-airway-inflammatory drug, and it can act on many aspects of asthma. But 80% patients respond well to adrenal cortical hormone, while 20% percent patients do not because of decreased number of receptor for adrenal cortical hormone on the cell surface of patient. Systemic therapy with hormone induces easily the inhibition of hypothalamic-pituitary-adrenal axis, which may cause the patents dependent on hormone, and latent inflammation diffusion. For most patents, if hormone is inhaled more than 1600 ug per day for three months, their hypothalamic-pituitary-adrenal axis will be inhibited and even the function of adrenal cortical hormone. When they stop to inhale hormone, asthma will easily recur. The inventor of the present invention made Ping Chuan Chong Ji from traditional Chinese medicines to treat asthma. The PCCJ can relieve or cease the attack of asthma, improve pulmonary function, regulate the immunological function, enhance T cells and decrease IgE, inhibit airway allergic reaction, relieve high sensitive state of airway and reduce side effect and administrating dose of hormone, and even finally, make patients ceasing the administration of hormone. The effective rate of PCCJ is clinically 93%. To further prove the clinical efficacy, the clinical trials were made in Tel-ashomer hospital of Israel, the results are showed as follows.

A. Method

Subject: Outpatients suffered from asthma attack. The asthma was classified as the type of lung-heat with deficiency in organ and excess in superficiality in traditional Chinese medicine. The standards of diagnosis and judgment in the condition of the patient are in accordance with "Principle of Clinical Study of New Drugs (Chinese drug)".

After a two-week's run-in period of treatment with placebo, 28 patients were divided into two groups randomly. Double-blind and placebo-controlled study was conducted to evaluate the clinical efficacy of PCCJ in terms of symptom scores, morning and evening PF and changes of immunoregulatory function. There were 15 patients in test group, 12 females and 3 males, with the average age of 43 (19-68) years old and the average duration of disease of 20.5 years, including 1 patient with mild asthma, 13 patients with moderate asthma and 1 patient with serious asthma. Among the patients of the test group, there were 4 patents with endogenous asthma, 4 patients with exogenous asthma and 7 patients with mixed type of asthma. There were 13 patients in the control group, 7 females and 6 males, with the average age of 46(18-68) years and the average duration of disease of 18.5 years, including 3 patients with mild asthma, 9 patients with moderate asthma and 1 patient with serious asthma. Among the patients of the test group, there were 4 patients with endogenous asthma, 4 patients with exogenous asthma and 5 patients with mixed type of asthma.

B. Trial Design

This trial is conducted using two groups of patients in a double-blind, randomized, parallel-grouped manner. It was carried out in Tel-Hashomer hospital of Israel. All patients agreed to conduct the trial by witnessed oral and written form.

The trial includes a 2 weeks' run-in period (period 1), a 4 weeks' controlled period (period 2), a 4 weeks' titration period (period 3) and a 4 weeks' open period (period 4). There were 6 scheduled visits to the clinic: at the start of run-in period, at the start of the treatment, 2 weeks after the treatment, and then 4, 6, 8 and 10 weeks after the treatment.

All patients entering the run-in phase received placebo at a dose of 5 capsules per time, 3 times daily, and if necessary, administrated additionally western medicine. At the end of the run-in period, the patients were randomly assigned to receive either of the following treatments, administrating PCCJ or placebo (5 capsules for each agent, 3 times daily) for a period of two months.

The whole trial was designed to divide into stages A, B, C, D. A: 2 weeks' run-in period, all patients took placebo together with conventional western medicine; B: 4 weeks' treatment period, the patients took PCCJ or placebo together with conventional western medicine; C: 4 weeks' treatment period, the patients did their best to reduce the dosage of conventional western medicine; D: the patients in the control group were given PCCJ for one month.

C. Diary-Card Data

Patients filled in a daily diary during the run-in and treatment periods, recording the better value of peak expiratory flow before administration in the morning and evening detected with a standard pneumatometer; Symptoms of asthma during the night or the daytime (based on scoring with 5 scales with 0 indicating no symptom and more than 3 representing severe symptom); the times of awakening due to asthma; the times and dosage of inhaling hormones and bronchodilator (including those at night and those during daytime); and the dosage of the western medicines given by oral route.

D. Clinic Visits

At each of the scheduled clinic visits, questionnaire included emotional status and asthma symptoms, including coughing, phlegm and dyspnea, some clinical measures, including rale of lung, the heart rates (HR) and blood pressure (BP); adverse effects; withdrawals from the trial, or reducing and stopping the administration of western medicines. Diary cards were reviewed, and lung function (FVC, FEV1, and FEV1%) were measured with the lung function instrument. In addition, IgE, cholesterol and blood count were detected too.

Episode-Free Days

An episode-free day was a day of optimally controlled asthma. That is to say, it is not necessary to inhale any hormone and bronchodilator, the score of asthma symptom was 0, peak expiratory flow appeared in morning was up to 80 percent and there is no adverse event.

E. Treatment

In the test group, the patients took Ping Chuan Chong Ji orally. PCCJ is not only a symptom-treating drug but also a cause-treating drug, containing *EPHEDRA SINICA,* *PERILLA FRUTESCENS,* *PRUNUS ARMENIACA,* *CODONOPSIS PILOSULA* etc. 5 capsules each time, 3 times daily. One course of treatment consists of 2 months. The patients in the control group took placebo, 5 capsules each time, 3 times daily. One course of treatment consists of two months. The patients with serious asthma were given additionally hormone.

F. Statistical Analysis

The date analysis followed a factorial design, and pairwise comparisons were made by t test and ANOVA.

G. RESULTS 28 patients were randomly divided into two groups. The differences of symptoms, pulmonary function, PF and so on in base-line date between the groups were minor and non-significant. There were 15 and 13 patients in the treatment group and the control group, respectively. In the control group, 2 patients were given additionally hormone because of worsening asthma. However, in the treatment group, no patient was given additionally hormone, and reduce the dosage of hormone easily and even some of them completely stop the administration of hormone without recurrence found by following up for half year after the trial.

H. The Judgment Standard of Curative Effects

Clinically controlled: the asthma's symptom and the wheeze vanish or become less than the mild degree; markedly effective: the asthma's symptom and the wheeze are improved significantly (+++−+); effective: the asthmatic symptom and the wheeze are improved slightly (+++−++−+); ineffective: the asthmatic symptom and the wheeze are not improved or even exacerbated.

I. The clinical Curative Effects

In the test group (PCCJ group), 3 cases (20%) were clinically controlled, 5 cases (33%) were markedly effective; 6 cases (40%) were effective and 1 case (7%) was ineffective. In control group, 6 cases (46%) were effective and 7 cases (54%) were ineffective. The total effective rate was 93% in the test group and 46% in the control group. A significant difference was founded between the two groups ($P<0.05$).

Symptom

1. Cough, Phlegm, Short of Breath and Wheeze

At the end of the run-in period, the patients received 5 capsules, 3 times per day. As a result, the scores of the clinical symptom in PCCJ group were significantly decreased, while no improvement was found in control group (table 1).

TABLE 1

The changes of cough, phlegm, shortness of breath, and wheeze's scores (mean ±SE)

| Groups | N | Symptoms | Period 1 (run-in) (score) | Period 2 (controlled) (score) | Period 3 (titration) (score) |
|---|---|---|---|---|---|
| PCCJ | 15 | cough | 1.600 ± 0.235 | 0.333 ± 0.126* | 0.200 ± 0.145* |
| | 15 | phlegm | 1.533 ± 0.236 | 0.400 ± 0.131* | 0.200 ± 0.107* |
| | 15 | short of breath | 2.200 ± 0.175 | 0.733 ± 0.248* | 0.53 ± 0.256* |
| | 15 | wheeze | 1.467 ± 0.274 | 0.333 ± 0.187* | 0.267 ± 0.206* |

TABLE 1-continued

| | | | Period 1 (run-in) | Period 2 (controlled) | Period 3 (titration) |
|---|---|---|---|---|---|
| Groups | N | Symptoms | (score) | (score) | (score) |
| control | 13 | cough | 1.154 ± 0.249 | 1.385 ± 0.385 | 1.462 ± 0.386 |
| | 13 | phlegm | 1.250 ± 0.231 | 1.154 ± 0.274 | 1.231 ± 0.303 |
| | 13 | short of breath | 2.143 ± 0.340 | 1.714 ± 0.286 | 2.143 ± 0.340 |
| | 13 | wheeze | 0.846 ± 0.249 | 1.000 ± 0.3 | 0.923 ± 0.288 |

Notes:

*$p < 0.0001$, compared with period 1 (run-in period).

2. Symptoms of Day and Night

Compared to those in the control group, the symptoms during the day and night were controlled very significantly in the PCCJ group (table 2).

TABLE 2

The changes of the symptoms' score of day and night (mean ±SE)

| Groups | N | symptoms | period 1 (run-in) (score) | period 2 (controlled) (score) | period 3 (titration) (score) |
|---|---|---|---|---|---|
| PCCJ | 15 | day | 3.133 ± 0.350 | 0.600 ± 0.190* | 0.400 ± 0.214* |
| | 15 | night | 1.933 ± 0.483 | 0.333 ± 0.187* | 0.133 ± 0.091* |
| control | 13 | day | 2.846 ± 0.355 | 2.615 ± 0.401 | 2.923 ± 0.431 |
| | 13 | night | 1.769 ± 0.455 | 1.462 ± 0.447 | 2.154 ± 0.478 |

Notes:

*$p < 0.0001$, compared with period 1 (run-in period).

3. Lung Function

FVC was increased significantly in PCCJ group during the treatment, while no improvement was found in the control group. The mean FEV1 of the base line was 51.8%, however, two weeks after administration and one month after administration, it was increased up to 64.133% and 65.867%, respectively. But the control group had no improvement (table 3).

4. Peak Expiratory Flow Rates

The peak expiratory flow rate was increased from 25 liters per minute before administration to 33.6 liters per minute in PCCJ group ($P<0.0001$), and no improvement was found in the Control group (table 4).

TABLE 3

The changes of FVC (L%) and FEV1 (L/S %) (mean ±SE)

| Groups | N | lung function | period 1 (run-in) | period 2 (controlled) | period 3 (titration) |
|---|---|---|---|---|---|
| PCCJ | 15 | FVC | 64.867 ± 4.412 | 79.600 ± 3.169** | 79.800 ± 3.468** |
| | 15 | FEV1 | 51.800 ± 5.170 | 64.133 ± 4.634* | 65.867 ± 4.895* |
| Control | 13 | FVC | 75.154 ± 6.214 | 76.385 ± 6.447 | 74.467 ± 5.760 |
| | 13 | FEV1 | 63.231 ± 7.322 | 64.000 ± 7.476 | 61.615 ± 6.479 |

Notes:

*$p < 0.0015$;

**$p < 0.0003$, compared with period 1 (run-in period).

TABLE 4

The changes of Peak Expiratory Flow Rates (mean ±SE)

| groups | N | lung function | period 1 (run-in) (M) | period 2 (controlled) (M) | period 3 (titration) (M) |
|---|---|---|---|---|---|
| PCCJ | 15 | PF | 250 ± 14.768 | 330.667 ± 19.085* | 336 ± 18.434* |
| Control | 13 | PF | 299.231 ± 35.018 | 290 ± 30.530 | 294.615 ± 30.668 |

Notes:
*p < 0.0001, Compared with period 1 (run-in period).

5. The change of IgE

IgE was lowered only in PCCJ group rather than the control group (table 5).

TABLE 5

The change of IgE (mean ±SE)

| groups | N | IgE | period 1 (run-in) (IU/ML) | period 2 (controlled) (IU/ML) |
|---|---|---|---|---|
| PCCJ | 14 | IgE | 193.931 ± 41.4 | 120.380 ± 24.93* |
| Placebo | 10 | IgE | 286.706 ± 68.142 | 304.229 ± 71.699 |

Notes:
*p < 0.067, compared with period 1 (run-in period).

6. Cholesterol

PCCJ was able to reduce the level of cholesterol in the blood, while the level of cholesterol in control was not changed significantly (table 6).

TABLE 6

The change of the level of cholesterol in blood (mean ±SE)

| groups | N | cholesterol | period 1 (run-in) (mg %) | period 2 (controlled) (mg %) |
|---|---|---|---|---|
| PCCJ | 15 | cholesterol | 226.067 ± 10.882 | 211.067 ± 9.737* |
| Control | 11 | cholesterol | 205.455 ± 13.003 | 207.091 ± 15.589 |

Note:
*p < 0.0073, compared with period 1 (run-in period).

7. The PCCJ Significantly Reduced the Attack of Asthma

TABLE 7

The changes of asthma's attack (mean ±SE)

| Groups | N | period 1 (run-in) (score) | period 2 (controlled) (score) | period 3 (titration) (score) |
|---|---|---|---|---|
| PCCJ | 15 | 2.4 ± 0.335 | 0.4 ± 0.190* | 0.333 ± 0.159* |
| Control | 13 | 2.308 ± 0.398 | 2.154 ± 0.436 | 2.308 ± 0.365 |

Note:
*P < 0.0001, compared with period 1 (run-in period).

8. PCCJ Reduced the Administrating Dosage of Ventolin (salbutamol)

TABLE 8

The change of the dosage of Ventolin (mean ±SE)

| groups | N | period 1 (run-in) puff (100 μg) | period 2 (controlled) puff (100 μg) | period 3 (titration) puff (100 μg) |
|---|---|---|---|---|
| PCCJ | 15 | 3.667 ± 0.583 | 1.267 ± 0.396* | 0.667 ± 0.252* |
| Control | 12 | 3.417 ± 0.811 | 3.167 ± 0.878 | 3.333 ± 0.762 |

Note:
*p < 0.0001, compared with period 1 (run-in period).

9. The PCCJ Reduced the Dosage of Flixotide

TABLE 9

The change of the dosage of Flixotide (Mean ±SE)

| Groups | N | Period 1 (run-in) (μg) | Period 2 (controlled) (μg) | Period 3 (titration) (μg) |
|---|---|---|---|---|
| PCCJ | 7 | 714.286 ± 101.015 | 178.571 ± 89.879* | 250 ± 77.152* |
| Control | 11 | 318.182 ± 71.060 | 363.636 ± 91.476 | 386.364 ± 91.476 |

Note:
*p < 0.0038, compared with period 1 (run-in period).

10. PCCJ Reduced the Dosage of Budicort (table 10).

TABLE 10

The change of the dosage of Budicort (mean ±SE)

| Groups | N | Period 1 (run-in) (mg) | Period 2 (controlled) (mg) | Period 3 (titration) (mg) |
|---|---|---|---|---|
| PCCJ | 11 | 0.455 ± 0.61 | 0.218 ± 0.078* | 0.127 ± 0.041* |
| Control | 11 | 0.218 ± 0.063 | 0.2 ± 0.060 | 0.273 ± 0.078 |

Note:
*p < 0.0001, compared with period 1 (run-in period).

11. PCCJ Reduced the Dosage of Serevant (table 11).

TABLE 11

The changes of the dosage of Serevant (mean ±SE)

| Groups | N | Period 1 (run-in) (µg) | Period 2 (controlled) (µg) | Period 3 (titration) (µg) |
|---|---|---|---|---|
| PCCJ | 9 | 23.000 ± 3.391 | 16.000 ± 3.279* | 15 ± 1.5* |
| Control | 10 | 15.3 ± 4.253 | 15.3 ± 4.253 | 14.4 ± 4.285 |

Note:
*p < 0.0661, compared with period 1 (run-in period).

12. PCCJ was able to Regulate the T Cell Subgroup.

TABLE 12

The changes of T Cell Subgroup before and after Treatment (mean ±SD)

| Groups | | N | CD2 (%) | CD4 (%) | CD8 (%) | CD4/CD8 |
|---|---|---|---|---|---|---|
| healthy person | | 10 | 83 ± 6.9 | 58.8 ± 6.3 | 25.9 ± 2.6 | 2.2 ± 0.25 |
| PCCJ | before treatment | 25 | 56.4 ± 11.6$^\Delta$ | 32.1 ± 11$^\Delta$ | 40.6 ± 14.1$^\Delta$ | 0.9 ± 0.4$^\Delta$ |
| | after treatment | 25 | 65.3 ± 14* | 47.5 ± 12.5* | 27.5 ± 5* | 1.8 ± 0.34** |
| Control | before treatment | 8 | 50.3 ± 6.4$^\Delta$ | 37 ± 8.5$^\Delta$ | 36.1 ± 10.1$^\Delta$ | 1.2 ± 0.6$^\Delta$ |
| | after treatment | 8 | 48 ± 6.3 | 36 ± 11.4 | 32.6 ± 15.1 | 1.3 ± 0.65 |

Note:
compared with healthy person$^\Delta$, P < 0.01; compared with before treatment,
*P < 0.05;
**p < 0.01.

The results showed that before treatment, the percents of $CD_2$ and $CD_4$ in two groups were lower than those of the healthy people, the percents of $CD_8$ were higher than those of the healthy people and the ratios of $CD_4/CD_8$ were lower than those of the healthy people. This suggested that during acute asthma attack, the patients had the disorder of T cell subgroups. After treatment, $CD_2$, $CD_4$ and the ratio of $CD_4/CD_8$ were increase significantly, while $CD_8$ was lowered. However, no significant change was found in the control group.

Discussion

The observations proved that the PCCJ was able to relax the smooth muscle of bronchus, which was useful to treat the acute attack of asthma and exert the function of anti-airway allergic inflammation to cease the attack of asthma. At the same time, the Chinese herbal medicines tonifying kidney also prevented the asthma's attack. T lymphocyte subgroups play an important regulative role in hormonal immunity. In recent years, it is was found that T cell regulated the formation of IgE, and when lymphocytes were cultured, $T_H$ clone prompted B cell to secret more IgE. Some patients belong to the IgE-dependent type, who has a higher level of IgE in blood serum, and IgE results in the releasing of mediator after mast cells have been cross-linked, which brings about bronchospasm or acute attack. In the meantime, it was also found that patients of asthma have a decreased $T_H$ in the peripheral blood and a increased $T_H$ in the lung tissue, and it lasted for a long time. This suggested that $T_H$ migrated to lung and played an important role in the production of type 1 allergic reaction. PCCJ was able to regulate T cell subgroups and prevented the attack of asthma, and increased CAMP in plasma, protected and increased lung cells type 2, and recovered the lung function to the normal level. Moreover, it was also able to reduce the dosage or even stop the administration of hormone. The animal experiment showed that PCCJ had no side effects even if it was took with 214 times dosage as high as the normal for 1 week and 80 times dosage for 3 months. So long term use of the drug of the present invention can treat the asthma efficiently and safely.

THE SPECIFIC MODE FOR CARRYING OUT THE INVENTION

The Chinese herbal medicines used in each prescription are available commercially in China. The various medicinal herbs were weighed according to the herbs employed and their percentage showed in the prescription, and then ground to powder, which encapsulated into capsule, 0.5 g per capsule.

The invention claimed is:

1. A composition for treatment of asthma, the composition comprising:

| Name (pinyin) | Latin Name (species) | % amount (w/w) |
|---|---|---|
| XING REN | PRUNUS ARMENIACA | approximately 1-30%; |
| GAN CAO | GLYCYRRHIZA URALENSIS | approximately 1-30%; |
| HUANG QIN | SCUTELLARIA BAICALENSIS | approximately 1-35%; |
| HUANG LIAN | COPTIS CHINENSIS | approximately 1-35%; |
| BAI BU | STEMONA SESSILIFOLIA | approximately 1-30%; |
| CHUAN BEI MU | FRITILLARIA CIRRHOSA | approximately 1-30%; |

-continued

| Name (pinyin) | Latin Name (species) | % amount (w/w) |
|---|---|---|
| DI LONG | PHERETIMA ASPERGILLUM | approximately 1-35%; |
| BU GU ZHI | PSORALEA CORYLIFOLIA | approximately 1-30%; |
| DANG SHEN | CODONOPSIS PILOSULA | approximately 1-30%; |
| SHAN ZHA | CRATAEGUS PINNATIFIDA | approximately 1-30%; |
| MAI YA | HORDEUM VULGARE | approximately 1-30%; |
| SHEN QU | MASSA FERMENTATA MEDICINALIS | approximately 1-30%; |
| WU WEI ZI | SCHISANDRA CHINENSIS | approximately 1-30%; |
| SHI GAO | GYPSUM | approximately 5-50%; and, |
| SU ZI | PERILLA FRUTESCENS | approximately 1-30%. |

2. The composition for treatment of asthma according to claim 1, the composition comprising:

| Name (pinyin) | Latin Name (species) | % amount (w/w) |
|---|---|---|
| MA HUANG | EPHEDRA SINICA | approximately 1-10%; |
| XING REN | PRUNUS ARMENIACA | approximately 1-10%; |
| GAN CAO | GLYCYRRHIZA URALENSIS | approximately 1-10%; |
| HUANG QIN | SCUTELLARIA BAICALENSIS | approximately 1-10%; |
| HUANG LIAN | COPTIS CHINENSIS | approximately 1-15%; |
| HUANG BAI | PHELLODENRON CHINENSE | approximately 1-15%; |
| KUANG DONG HUA | TUSILAGO FARFARA | approximately 1-10%; |
| BAI BU | STEMONA SESSILIFOLIA | approximately 1-10%; |
| CHUAN BEI MU | FRITILLARIA CIRRHOSA | approximately 1-10%; |
| DI LONG | PHERETIMA ASPERGILLUM | approximately 1-15%; |
| BU GU ZHI | PSORALEA CORYLIFOLIA | approximately 1-10%; |
| DANG SHEN | CODONOPSIS PILOSULA | approximately 1-10%; |
| SHAN ZHA | CRATAEGUS PINNATIFIDA | approximately 1-8%; |
| MAI YA | HORDEUM VULGARE | approximately 1-6%; |
| SHEN QU | MASSA FERMENTATA MEDICINALIS | approximately 1-6%; |
| WU WEI ZI | SCHISANDRA CHINENSIS | approximately 1-10%; |
| SHI GAO | GYPSUM | approximately 5-30%; and, |
| SU ZI | FERILLA FRUTESCENS | approximately 1-10%. |

3. The composition for treatment of asthma according to claim 2, the composition comprising:

| Name (pinyin) | Latin Name (species) | % amount (w/w) |
|---|---|---|
| MA HUANG | EPHEDRA SINICA | 5.1%; |
| XING REN | PRUNUS ARMENIACA | 6.12%; |
| GAN CAO | GLYCYRRHIZA URALENSIS | 5.1%; |

-continued

| Name (pinyin) | Latin Name (species) | % amount (w/w) |
|---|---|---|
| HUANG QIN | SCUTELLARIA BAICALENSIS | 6.12%; |
| HUANG LIAN | COPTIS CHINENSIS | 6.12%; |
| HUANG BAI | PHELLODENDRON CHINENSE | 6.12%; |
| KUANG DONG HUA | TUSILAGO FARFARA | 5.1%; |
| BAI BU | STEMONA SESSILIFOLIA | 5.1%; |
| CHUAN BEI MU | FRITILLARIA CIRRHOSA | 5.1%; |
| DI LONG | PHERETIMA ASPERGILLUM | 5.1%; |
| BU GU ZHI | PSORALEA CORYLIFOLIA | 5.1%; |
| DANG SHEN | CODONOPSIS PILOSULA | 6.1%; |
| SHAN ZHA | CRATAEGUS PINNATIFIDA | 4.12%; |
| MAI YA | HORDEUM VULGARE | 2.04%; |
| SHEN QU | MASSA FERMENTATA MEDICINALIS | 2.04%; |
| WU WEI ZI | SCHISANDRA CHINENSIS | 5.1%; |
| SHI GAO | GYPSUM | 15.31%; and, |
| SU ZI | PERILLA FRUTESCENS | 5.1%. |

4. A composition for treatment of asthma according to claim 1, the composition further comprising:

| Name (pinyin) | Latin Name (species) | % amount (w/w) |
|---|---|---|
| ZI WAN | ASTER TATARICUS | approximately 1-30%; |

5. The composition for treatment of asthma according to claim 4, wherein the composition further comprises:

| Name (pinyin) | Latin Name (species) | % amount (w/w) |
|---|---|---|
| BAI SHAO | PAEONIA LACTIFLORA | approximately 1-30%. |

6. The composition for treatment of asthma according to claim 5, wherein the composition is in a pharmaceutically acceptable dosage form.

7. The composition for treatment of asthma according to claim 4, wherein the composition is in a pharmaceutically acceptable dosage form.

8. The composition for treatment of asthma according to claim 1, wherein the composition further comprises:

| Name (pinyin) | Latin Name (species) | % amount (w/w) |
|---|---|---|
| BAI SHAO | PAEONIA LACTIFLORA | approximately 1-30%; |
| JIN YIN HUA | LONICERA JAPONICA | approximately 1-30%; |
| LIAN QIAO | FORSYTHIA SUSPENSA | approximately 1-30%; and, |
| JING JIE | SCHIZONEPETA TENUIFOLIA | approximately 1-30%. |

9. The composition for treatment of asthma according to claim 8, wherein the composition is in a pharmaceutically acceptable dosage form.

10. The composition for treatment of asthma according to claim 1, wherein the composition is in a pharmaceutically acceptable dosage form.

* * * * *